United States Patent [19]

Miller et al.

[11] Patent Number: 4,487,982
[45] Date of Patent: Dec. 11, 1984

[54] INHIBITING POLYMERIZATION OF VINYL AROMATIC MONOMERS

[75] Inventors: Richard F. Miller, Humble; Michael P. Nicholson, Houston, both of Tex.

[73] Assignee: Atlantic Richfield Company, Los Angeles, Calif.

[21] Appl. No.: 530,443

[22] Filed: Sep. 8, 1983

[51] Int. Cl.³ .............................................. C07C 7/18
[52] U.S. Cl. ........................................... 585/4; 585/5; 585/441; 585/864; 585/952; 544/35; 544/37
[58] Field of Search ...................... 585/2, 3, 4, 5, 864, 585/865, 866, 867, 952; 544/35, 37

[56] References Cited

U.S. PATENT DOCUMENTS

| | | | |
|---|---|---|---|
| 2,361,538 | 10/1944 | Franz | 585/5 |
| 2,402,113 | 6/1946 | Hatch et al. | 585/5 |
| 2,867,672 | 1/1959 | Hammerich | 585/4 |
| 3,347,938 | 10/1967 | Bell et al. | 585/3 |
| 3,390,198 | 6/1968 | Leston | 585/3 |
| 3,539,515 | 11/1970 | McCabe | 252/47.5 |
| 3,689,484 | 9/1972 | Spilners | 544/35 |
| 3,956,289 | 5/1976 | McGuigen et al. | 544/37 |
| 4,177,110 | 12/1979 | Watson | 585/5 |
| 4,409,408 | 10/1983 | Miller | 585/4 |
| 4,661,545 | 12/1977 | Watson | 585/864 |

FOREIGN PATENT DOCUMENTS 4034641 8/1970 Japan ..................... 585/4

Primary Examiner—Delbert E. Gantz
Assistant Examiner—A. Pal
Attorney, Agent, or Firm—C. R. Reap; D. M. Kozak; J. C. Martin, Jr.

[57] ABSTRACT

Vinyl aromatic compounds are stabilized against undesired polymerization by adding to the vinyl aromatic compounds small amounts of at least one N,N' dimer of phenothiazine or a substituted phenothiazine and at least one mono- or ditertiary alkylphenol.

10 Claims, No Drawings

INHIBITING POLYMERIZATION OF VINYL AROMATIC MONOMERS

FIELD OF THE INVENTION

The present invention relates to the stabilization of ethylenically unsaturated compounds and more particularly to the inhibition of undesired polymerization of vinyl aromatic compounds during storage, shipping or processing.

BACKGROUND

Vinyl aromatic compounds such as styrene undergo undesired spontaneous polymerization (i.e. polymerization of monomers due to heat or the random generation of free radicals in the monomers) during storage, shipping or processing. The problem is particularly acute during purification operations carried out at elevated temperatures such as distillation. Spontaneous polymerization is disadvantageous not only because it causes fouling of distillation column reboilers and other equipment used for processing the vinyl aromatic monomer but also because it usually renders the monomer unfit for use without further treatment. Accordingly, it is desirable and often necessary to inhibit the spontaneous polymerization of vinyl aromatic monomers.

PRIOR ART

To prevent spontaneous polymerization of vinyl aromatic monomers it is common practice to add to the monomers compounds which have polymerization inhibiting activity. A wide variety of such compounds, known as polymerization inhibitors, have been used for this purpose. Sulfur has been widely used in the past to inhibit polymerization of vinyl aromatic compounds; however, sulfur usage is undesirable because large quantities of sulfur are required for effective polymerization inhibition. This presents a waste removal problem when the monomer is separated from the sulfur-monomer mixture, which is accomplished by distillation. The distillation bottoms product, which contains higher molecular weight hydrocarbons, polymer and sulfur, cannot be burned due to the air pollution hazard caused by sulfur oxides. Thus, this material must be disposed of by burial in a waste dump.

In recent times, many chemical compounds have been developed as substitutes for sulfur in polymerization inhibiting applications. These compounds have been used as polymerization inhibitors for vinyl aromatic monomers with varying degrees of success. U.S. Pat. No. 3,390,198, issued to Leston, discloses the use of several mono- and dialkylcatechols as polymerization inhibitors for hot styrene. U.S. Pat. No. 2,361,538 discloses the use of certain phenolic compounds to inhibit polymerization of vinyl compounds. U.S. Pat. No. 4,061,545 and 4,177,110 issued to Watson, disclose the use of a combination of tertiary-butylcatechol and phenothiazine as a polymerization inhibitor system for vinyl aromatic compounds. U.S. Pat. No. 3,539,515, issued to McCabe, discloses the use of phenothiazine dehydrocondensates as antioxidants for lubricating oils. The phenothiazine dehydrocondensates are prepared by reacting phenothiazine or a substituted phenothiazine with an organic peroxide.

It has now been discovered that mixtures of N,N' dimers of phenothiazine or substituted phenothiazine and mono- or dialkylphenols provide outstanding polymerization inhibiting activity for vinyl aromatic monomers. Thus, now possible to provide unexpectedly superior polymerization inhibiting protection with the same total equivalent weight of mixtures of the N,N' dimers of phenothiazine or substituted phenothiazines and mono- or dialkylphenols than is obtainable by the use of members of either of these groups of compounds by themselves.

Accordingly, it is object of the invention to present stable compositions of vinyl aromatic monomers. It is another object of the invention to present a method of effectively and economically inhibiting spontaneous polymerization of styrene and other vinyl aromatic monomers. These and other objects of the invention are set forth in the following description and examples of the invention.

SUMMARY OF THE INVENTION

According to the invention the protection of vinyl aromatic monomers against spontaneous polymerization is accomplished by incorporating into the monomers a polymerization inhibiting system comprised of at least one N,N' dimer of phenothiazine or a substituted phenothiazine and one or more mono- or dialkylphenols, each alkyl group of which has 1 to 20 carbon atoms.

DETAILED DESCRIPTION OF THE INVENTION

The term vinyl aromatic monomer as used in this description includes any of the readily polymerizable vinyl aromatic compounds, e.g. styrene, alpha alkyl styrene, such as alpha methyl styrene, ring alkyl-substituted styrene such as p-methyl styrene, diethylenically-substituted benzene compounds, such as divinylbenzene, etc. and mixtures thereof.

The N,N' dimers of phenothiazine or the substituted because of the synergistic effect of these mixtures it is phenothiazine most useful in the invention have the structural formula

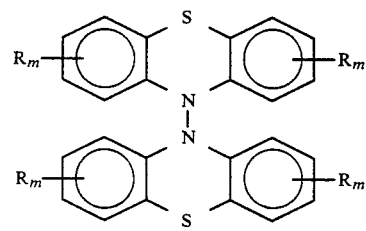

wherein m is an integer of 0 to 4, i.e. there may be from 0 to 16 R substitutents on each molecule of the dimer, and some or all of the R's may be identical or all of the R's may be different. In the preferred embodiment the m's are integers having values of 0, 1 or 2. Each R may be a halogen atom or an unsubstituted or a halogen-substituted alkyl group having 1 to 20 and preferably 1 to 6 alkyl carbon atoms.

When all of the m's in the above structural formula are 0, the compound is the N,N' dimer of phenothiazine. This is the preferred dimer for use in of the invention since unsubstituted phenothiazine is less expensive as a starting material than the substituted phenothiazines. In an alternate embodiment the m's may be integers of 1 to 4, in which case the compound is a dimer of an alkyl-substituted or haloalkyl-substituted derivative of phenothiazine. Typical hydrocarbon alkyl substituents include methyl, ethyl, isopropyl, butyl, hexyldecyl, hexadecyl, etc. groups. There may be up to 4 such substituents on each benzene ring portion of the dimer. Since the dimer contains 4 benzene nuclei there may be up to 16 identical or different substituents. If all of the phenothiazine component starting material is phenothiazine or a single derivative of phenothiazine, the dimer is composed of two identical moieties. However, if the phenothiazine component starting material is composed of two or more different phenothiazine derivatives a mixture of products would result some of which could have 16 different substituents if the monomeric starting materials had all dissimilar substituents.

Typical phenothiazine dimers are 10,10'diphenothiazine; 1,1'-dimethyl-10,10'diphenothiazine; 2,6,2'6'tetramethyl-10,10'-diphenothiazine; 2,2'-dimethyl-8,8'dipropyl-10,10'diphenothiazine; 3,4'-dimethyl,6,7'dihexyl-10,10'-diphenothiazine; 2,2'-dichloro-10,10'-diphenothiazine; 3,3',7,7'-tetrabromo-10,10'diphenothiazine; 4,4'-bis(2-chloroethyl)-10,10'-diphenothiazine; 3,3',6,6'-tetrakis(4-fluorobutyl)-10,10'-diphenothiazine; 1,1',2,2',3,3',4,4',6,6',7,7',8,8',9,9' hexadecylmethyl-10,10'-diphenothiazine; etc. From the standpoint of preparation, cost and utility, the preferred phenothiazine dimers are phenothiazine dimer and the alkyl-substituted phenothiazine dimers up to two substituents on each benzene nucleus, each substituent having 1 to 4 carbon atoms in each alkyl group. Examples of preferred substituted phenothiazine dimers are 1,1'-dimethyl-10,10'-diphenothiazine, 2,2'-dimethyl-4,4'-diethyl-10,10'-diphenothiazine; 2,2',6,6'-tetramethyl-3,3'-diethyl-10,10'-diphenothiazine, etc.

The term "phenothiazine component" as used herein represents phenothiazine or any of the substituted phenothiazines included in the above definition.

Phenothiazine and some hydrocarbon-substituted phenothiazines are available commercially. Others may be prepared by well-known techniques, such as alkylation. The preparation of the phenothiazine component forms no part of the present invention.

The phenothiazine dimers used in the invention are prepared by heating the phenothiazine component in the presence of an organic peroxide. The optimum reaction temperature employed will vary depending upon the particular phenothiazine compound used as the starting material and the particular organic peroxide used. In general, temperatures in the range of about 25° to 300° C. are effective to produce the desired result.

Any of the common organic peroxides can be used to effect the dimerization. The peroxide chosen will depend upon the desired reaction temperature. Typical organic peroxides include benzoyl peroxide, lauroyl peroxide, ditertiary-butyl peroxide, tertiary-butyl hydroperoxide, tertiary-butyl peroctoate, acetyl peroxide, etc.

The amount of peroxide present in the reactor relative to the amount of phenothiazine component in the reactor will determine the rate of reaction. Uaually it is preferred to add the peroxide to the reactor containing the charge of phenothiazine component at a controlled rate to maintain the reaction speed at the desired rate. The amount of peroxide in the reactor is usually maintained in the range of about 1 to 50 mole percent and preferably in the range of about 5 to 25 mole percent, based on the total number of moles of phenothiazine component present in the reactor.

The dimers can be prepared by heating the phenothiazine component and organic peroxide directly, but since the phenothiazine component and many organic peroxides are solid, it is usually preferable to carry out the reaction in the presence of a solvent or diluent. Typical diluents include the lower alkanes; petroleum distillate; kerosene; ketones, such as methyl ethyl ketone; aldehydes, such as benzaldehyde, etc. Ideally the solvent or diluent is a substance which will not interfere with the intended end use of the product so that there will be no need to recover the dimer from the solvent or diluent prior to the end use. When the reaction is carried out in the presence of a solvent or a diluent, the solvent or diluent is generally present in amounts of about 70–97%, based on the total weight of components in the reaction mixture.

In a typical procedure for preparing the dimers used in the invention the phenothiazine component and solvent or diluent are charged to a suitable reactor. The desired amount of organic peroxide is then charged to the reactor and the reactor contents are heated to the reaction temperature. If desired, the reaction may be carried out under a nitrogen blanket. As the peroxide is consumed additional peroxide is added to the reactor, either continuously or incrementally, at a rate of control the progress of the reaction. Since the reaction is exothermic it may be necessary to cool the reactor during the course of the reaction. It is usually complete in about 2 to 24 hours, depending, of course, on the reaction conditions. Excess peroxide may be added to the reactor to ensure that all of the phenothiazine component is reacted. Upon completion of the reaction, the product may be recovered from the solvent or used as is.

The mono- and dialkyl-substituted phenols useful in the invention have the structural formula

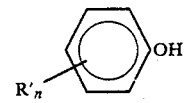

wherein R' is an alkyl group having 1 to 20 and preferably 4 to 12 carbon atoms and n is an integer having a value of 1 or 2. The preferred alkyl substituents are the tertiary alkyl groups.

Examples of mono- and dialkyl-substituted phenols useful in the invention are 2-methylphenol; 3-methylphenol; 2-ethylphenol; 4-t-butylphenol; 2-t-octylphenol; 4-dodecylphenol; 3-t-hexadecylphenol; 4-eicosylphenol; 2,4-dimethylphenol; 2,6-dimethylphenol; 2,4-di-t-butylphenol; 3,4-di-t-butylphenol; 3,5-di-t-butylphenol; 2,3-di-t-hexylphenol; 2,4-dodecylphenol; 2,6-di-t-dodecylphenol; 2,5-di-t-hexadecylphenol; 2,6-dieicosylphenol; 2-methyl-4-t-butylphenol; 2-hexyl-6-t-butylphenol, etc. Examples of preferred mono- and dialkylphenols include 2-methylphenol; 4-t-butylphenol; 2,4-di-octylphenol; 2,6-di-t-butylphenol; 2,4-dooctylphenol; 2,6-di-t-dodecylphenol; 3,5-dihexylphenol; etc.

In some cases it may be desirable to use mixtures of one or more mono- and/or dialkylphenols. Such mixtures are also within the scope of the invention.

Some mono- and dialkylphenols, such as di-t-butylphenol, are available commercially. Those mono- and dialkylphenols which are not commercially available may be prepared by any of the well known techniques. The preparation of these compounds forms no part of the present invention.

The relative concentrations of the N,N' dimer of the phenothiazine component and mono- and/or dialkylphenol used in the invention are generally in the range of about 10 to 90 weight percent of the N,N' dimer of the phenothiazine component and 90 to 10 weight percent total mono- and/or dialkylphenol, based on the total combined weight of these components. In preferred embodiments the concentrations generally fall in the range of about 25 to 75 weight percent of the N,N' dimer of the phenothiazine component and 75–25% total alkylphenol, based on the total combined weight of these components.

The polymerization inhibiting system of the invention is particularly well suited for protecting the reboiler sections of a distillation column during distillation of vinyl aromatic monomers because of the high boiling point of the inhibitor compounds in the system. The inhibitor system may be used at temperatures up to about 400° C. or higher at atmospheric pressure. Since the boiling point of various members of each of the two classes of compounds, i.e. the N,N' dimers of the phenothiazine component and the alkylphenols are different, compounds which have the desired boiling point can be easily selected from each class. To make up for the inhibitor which is left behind during distillation, additional inhibitor can be added to the vinyl aromatic monomer after it is distilled from heavier hydrocarbons. In some cases it may be desirable to use lower boiling polymerization inhibitors in combination with the inhibitor system of the invention. For example, when distilling a vinyl aromatic monomer from higher boiling hydrocarbons it may be advantageous to add a polymerization inhibitor which has a boiling point near or lower than the boiling point of the vinyl aromatic compound. This will provide protection to the overhead portion of the column. It may also be desirable to add with the polymerization inhibiting system of the invention other agents, such as corrosion inhibitors, to provide additional protection to process equipment.

The inhibitor system of the invention can be introduced into the monomer to be protected by any conventional method. It is generally introduced just upstream of the point of desired application by any suitable means, such as by the use of a proportionating pump. It can be added to the monomer as a single composition containing all of the desired inhibitor compounds, or the individual components can be added separately or in any other desired combination. The composition may be added as a concentrate, if desired, but it is preferable to add it as a solution which is compatible with the monomer being treated. Suitable solvents include kerosene, naphtha, the lower alkanes such as hexane, aromatic solvents such as toluene, alcohols, ketones, etc. It is often preferred to dissolve the inhibitors of the invention in the monomer to which the inhibitor is being added to avoid introducing additional impurities to the monomer. The concentration of inhibitor system in the solvent is desirably in the range of about 1 to 30 weight percent and preferably about 5 to 20 weight percent based on the total weight of inhibitor and solvent.

The polymerization inhibitor system is used at a concentration which is effective to provide the desired protection against spontaneous polymerization. It has been determined that amounts of inhibitor in the range of about 0.5 to 1000 ppm based on the weight of the monomer being treated affords ample protection against undesired polymerization. For most applications the inhibitor system is used in amounts in the range of about 5 to 500 ppm.

The components of the polymerization inhibiting system can be easily removed from the vinyl aromatic monomer prior to polymerization by caustic washing. Such procedures are well known and commonly practiced to separate phenolic type inhibitors, such as tertiary butylcatechol, from monomers.

The following examples will serve to further illustrate the invention. Unless otherwise stated, parts and percentages are on a weight basis. In the examples styrene, which is representative of vinyl aromatic monomers, was used as the test monomer.

EXAMPLE I (CONTROL)

To a 250 ml three neck reaction flask equipped with a stirrer, a thermometer, a Dean-Stark trap and a water-cooled condenser is charged 200 mls of styrene monomer. The monomer, while being maintained under a vacuum of 23.5 to 26 inches of Hg was heated to and maintained at a temperature in the range of 102° to 105° C. Total reflux was maintained for a period of fifteen minutes after which 100 ml of monomer was removed from the flask in several distillation cuts taken over a two hour period. The reactor contents were then cooled and a 10 ml sample of the reactor residue was drawn and tested to determine the amount of styrene polymer formed by the following procedure: a 10 ml sample of styrene monomer was introduced into 100 ml of cold methanol, to quench the polymerization reaction; the methanol-monomer mixture was heated sufficiently to coagulate the polymer formed; and the polymer was recovered from the methanol by filtration, dried overnight at a temperature of 100° F. and weighed. The percentage of polymer formed was determined and reported in the Table in the Run 1 row.

EXAMPLE II (COMPARATIVE)

The procedure and test of Example I were repeated except that 250 ppm of 2,4-di-t-butylphenol was added to the flask just prior to heating. The sytrene monomer was tested for polymer formation as indicated in Example I. The results are tabulated in the Table in the Run 2 row.

EXAMPLE III

To a 500 ml three neck flask equipped with a stirrer, a condenser and a thermometer was charged 200 grams of a 50:50 weight mixture of acetophenone and benzaldehyde and 199.28 grams of phenothiazine. The reaction mixture was stirred at 25° C. for 30 minutes and to this was added 199.3 grams of lauroyl peroxide at a rate of addition sufficiently slow to maintain the resultant exotherm below 35° C. The reaction was considered to be complete after two hours with the color of the initial reaction solution changing from a yellowish-green to a brilliant red. The reaction solvent was then removed from the product by evaporation. Mass spectral analysis showed the product to contain substantial amounts of 10,10'-diphenothiazine.

EXAMPLE IV (COMPARATIVE)

The procedure and test of Example II were repeated except that 250 ppm of the phenothiazine dimer prepared in Example III was substituted for the 2,4-di-t-butylphenol. The results are tabulated in the Table in the Run 3 row.

EXAMPLE V

The procedure of Example II was repeated except that 250 ppm of an inhibitor system comprised of 67 weight percent of di-t-butylphenol and 33 weight percent of the phenothiazine dimer prepared in Example III was used in place of the 2,4-di-t-butylphenol. The results are reported in the Table in the Run 4 below.

EXAMPLE VI

The procedure of Example V was repeated using 150 ppm of the di-t-butylphenol/phenothiazine dimer mixture. The results are reported in the Table in the Run 5 row.

EXAMPLE VII

The procedure of Example V was repeateld using 75 ppm of the di-t-butylphenol/phenothiazine dimer mixture. The results are reported in the Table in the Run 6 row.

TABLE

| Run | Inhibitor | Inhibitor Concentration, ppm | Weight % Polymer Formed |
| --- | --- | --- | --- |
| 1 | None | — | 10.30 |
| 2 | 2,4-di-t-butylphenol | 250 | 2.52 |
| 3 | 10,10'-diphenothiazine | 250 | 1.04 |
| 4 | di-t-butylphenol/ 10,10'-diphenothiazine | 250 | 0.09 |
| 5 | di-t-butylphenol/ 10,10'-diphenothiazine | 150 | 0.83 |
| 6 | di-t-butylphenol/ 10,10'-diphenothiazine | 75 | 1.48 |

The benefit of the use of the polymerization inhibitor compositions of the invention are shown in the Table. In the Table the uninhibited monomer contained 10.3 percent polymer after two hours of heating; the Run 2 monomer sample, which was inhibited by 250 ppm of 2,4-di-t-butylphenol, contained 2.52 percent polymer at the end of the two hour period and the two hour analysis of the Run 4 sample, which contained one of the inhibitors of the invention, a di-t-butylphenol/10,10'diphenolthiazine mixture, showed a polymer concentration of only 0.09 percent at the end of the two hour test period.

Although the invention is described with particular reference to specific examples, it is understood that the invention includes obvious variants. For example, the inhibitor system can be formulated to contain more than one dimer derivative of phenothiazine. The scope of the invention is limited only by the breadth of the claims.

What is claimed is:

1. A composition comprised of a vinyl aromatic compound and an amount effective to inhibit polymerization of said vinyl aromatic compound of
    (1) at least one member selected from N,N' dimers of phenothiazine, halo-substituted phenothiazines, alkyl-substituted phenothiazines and haloalkyl-substituted phenothiazines, and
    (2) at least one alkyl-substituted monohydroxy benzene.

2. A composition comprised of a vinyl aromatic compound containing, in an amount effective to inhibit polymerization of said vinyl aromatic compound, a mixture of
    (1) at least one compound having the structural formula

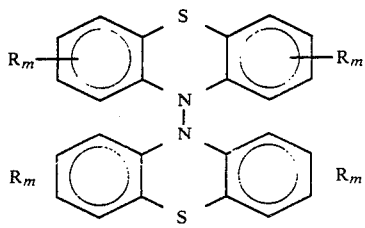

wherein the R's may be the same substituent or different substituents selected from alkyl groups having 1 to 20 carbon atoms, halogen atoms, halogen-substituted alkyl groups having 1 to 20 carbon atoms and mixtures of these and the m's may be the same integer or different integers in the range of 0 to 4,
    (2) at least one compound having the structural formula

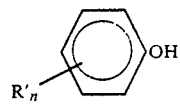

wherein R' is an alkyl group having a total of 1 to 20 carbon atoms and n is an integer having a value of 1 or 2.

3. The composition of claim 3 wherein the total concentration of the compounds in (1) and (2) in said composition is 0.5 to 1000 ppm, based on the total weight of vinyl aromatic compound and the relative concentration of the compounds in (1) and (2) are 90 to 10 parts by weight and 10 to 90 parts by weight respectively.

4. The composition of claim 2 wherein the vinyl aromatic compound is styrene or alkyl substituted styrene, the m's are the same or different integers selected from 0, 1 and 2, each R is an alkyl group having 1 to 6 carbon atoms, R'$_n$ is a tertiary alkyl group having have 4 to 8 carbon atoms, the relative concentrations of the compounds in (1) and (2) are 25 to 75 parts by weight and 75 to 25 parts by weight respectively and the total concentration of the compounds in (1) and (2) in said composition is 5 to 500 ppm, based on the total weight of vinyl aromatic compound.

5. The composition of claim 4 wherein the vinyl aromatic compound is styrene, the compound in (1) is 10,10-diphenothiazine and the compound in (2) is selected from tertiary butylphenol, ditertiary butylphenols and mixtures of these.

6. In a method of inhibiting polymerization of a vinyl aromatic compound comprising adding to the vinyl aromatic compound an amount of a polymerization inhibiting agent effective to substantially reduce the rate of polymerization, the improvement comprising using as the agent a combination of:
    (1) at least one member selected from the N,N' dimers of phenothiazine, halo-substituted phenothiazine, alkyl-substituted phenothiazines and haloalkyl-substituted phenothiazines, and
    (2) at least one alkyl-substituted monohydroxy benzene.

7. In a method of inhibiting polymerization of a vinyl aromatic compound comprising adding to the vinyl aromatic compound an amount of a polymerization inhibiting agent effective to substantially reduce the rate of polymerization, the improvement comprising using as the agent a combination of:

(1) at least one compound having the structural formula

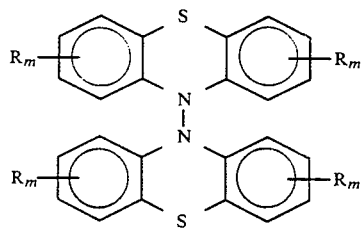

wherein the R's may be the same substituent or different substituents selected from alkyl groups having 1 to 20 carbon atoms, halogen atoms, halogen-substituted alkyl groups having 1 to 20 carbon atoms and mixtures of these and the m's may be the same integer or different integers in the range of 0 to 4, and (2) at least one compound having the structural formula

wherein R' is a an alkyl group having a total of 1 to 20 carbon atoms and n is an integer having a value of 1 or 2.

8. The process of claim 7 wherein the total concentration of the compounds in (1) and (2) in said composition is 0.5 to 1000 ppm, based on the total weight of vinyl aromatic compound and the relative concentration of the compounds in (1) and (2) are 90 to 10 parts by weight and 10 to 90 parts by weight respectively.

9. The process of claim 7 wherein the vinyl aromatic compound is styrene or alkyl substituted styrene, m is an integer selected from 0, 1 and 2, each R is an alkyl group having 1 to 6 carbon atoms, R' is a the tertiary alkyl group having 4 to 8 carbon atoms, the relative concentrations of the compounds in (1) and (2) are 25 to 75 parts by weight and 75 to 25 parts by weight respectively and the total concentration of the compounds in (1) and (2) in said composition is 5 to 500 ppm, based on the total weight of vinyl aromatic compound.

10. The process of claim 9 wherein the vinyl aromatic compound is styrene, the compound in (1) is 10,10'-diphenothiazine and the compound in (2) is selected from tertiary butylphenol, ditertiary butylphenols, and mixtures of these.

* * * * *

UNITED STATES PATENT AND TRADEMARK OFFICE
CERTIFICATE OF CORRECTION

PATENT NO. : 4,487,982

DATED : 12/11/84

INVENTOR(S) : R. F. Miller and M. P. Nicholson

It is certified that error appears in the above-identified patent and that said Letters Patent are hereby corrected as shown below:

Claim 3, column 8, line 32 "claim 3" should read --- claim 2 --.

Signed and Sealed this

Fourteenth Day of May 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,487,982
DATED : 12/11/84
INVENTOR(S) : R. F. Miller and M. P. Nicholson It is certified that error appears in the above-identified patent and that said Letters Patent is hereby corrected as shown below:

Claim 4, column 8, line 42 delete "have";

Claim 9, column 10, line 19 delete "the".

Signed and Sealed this

Second Day of July 1985

[SEAL]

Attest:

DONALD J. QUIGG

Attesting Officer     Acting Commissioner of Patents and Trademarks